(12) United States Patent
Schreiner et al.

(10) Patent No.: US 8,138,375 B2
(45) Date of Patent: Mar. 20, 2012

(54) METHOD FOR PRODUCING 1-FORMAMIDO-3,5-DIMETHYLADAMANTANE

(75) Inventors: Peter R. Schreiner, Wettenberg (DE); Andrey A. Fokin, Giessen (DE); Lukas Wanka, Wollstadt (DE); Derek M. Wolfe, Athens, GA (US)

(73) Assignee: MERZ PHARMA GmbH & Co. KGaA, Frankfurt am Main (DE)

( * ) Notice: Subject to any disclaimer, the term of this patent is extended or adjusted under 35 U.S.C. 154(b) by 521 days.

(21) Appl. No.: 12/224,575

(22) PCT Filed: Feb. 20, 2007

(86) PCT No.: PCT/EP2007/001433
§ 371 (c)(1),
(2), (4) Date: Jan. 13, 2009

(87) PCT Pub. No.: WO2007/101536
PCT Pub. Date: Sep. 13, 2007

(65) Prior Publication Data
US 2009/0299097 A1    Dec. 3, 2009

(30) Foreign Application Priority Data
Mar. 1, 2006 (DE) .......... 10 2006 009 279

(51) Int. Cl.
*C07C 231/08* (2006.01)
*C07C 233/57* (2006.01)
(52) U.S. Cl. .......... 564/222; 564/217; 564/460

(58) Field of Classification Search ............ 564/217, 564/222, 460
See application file for complete search history.

(56) References Cited

U.S. PATENT DOCUMENTS
5,061,703 A  10/1991  Bormann
5,117,056 A   5/1992  Listemann et al.

FOREIGN PATENT DOCUMENTS
DE  2318461     4/1973
EP  0392059     9/1993
WO  WO 2006/010362 A  2/2006

OTHER PUBLICATIONS

CN 1 566 075 (Xiaojun Zhang) Jan. 19, 2005, Chinese Language.
Database Caplus Chemical Abstracts Service; Columbus; Ohio; US; Oct. 19, 2005, Xiaojun Zhang: "Preparation of a substituted Symmetry Adamantane amine derivatives". XP002441200 Database accession No. AN:1117324—& CN 1 566 075 A (Xiaojun Zhang) Jan. 19, 2005, English abstract of Chinese Patent Application.
International Preliminary Report on Patentability with Written Opinion for PCT/EP2007/001433 of Oct. 23, 2008.
International Search Report for PCT/EP2007/001433 of Jul. 6, 2007.
Yu. N. Klimochkin et al., << Synthesis of alkoxycarbonylaminoadamantanes and acetylaminoadamantanes in nitric Acid >>, Bulletin of the Academy of sciences of the USSR vol. 37, No. 4, 1988, pp. 757-759, XP002441198 USSR, p. 759.
English translation of DE2318461, 1973.

*Primary Examiner* — Shailendra Kumar
(74) *Attorney, Agent, or Firm* — Hueschen and Sage

(57) ABSTRACT

The invention relates to a method for producing 1-formamido-3,5-dimethyladamantane in only two reaction steps by direct formamide formation of 1,3-dimethyladamantane, the 1,3-dimethyladamantane being reacted with formamide in concentrated acids.

4 Claims, No Drawings

METHOD FOR PRODUCING 1-FORMAMIDO-3,5-DIMETHYLADAMANTANE

This application is a 371 of PCT/EP2007/001433, filed Feb. 20, 2007.

Subject-matter of the invention is a method for preparing 1-formamido-3,5-dimethyladamantane, which is an important intermediate for the manufacture of 1-amino-3,5-dimethyladamantane that is used for the treatment of Alzheimer's disease and that is known under the agent name memantine. It is sold in Europe (and in numerous non-European countries) under the trademarks Axuras® and Ebixao® and under Namendae® in the USA.

The manufacture of 1-formamido-3,5-dimethyladamantane starting from 1-bromo-3,5-dimethyladamantane and formamide is already known as such.

1-amino-3,5-dimethyladamantane as substance is already known from DE 2 318 46 A1. Its use for prevention and treatment of cerebral ischemia is described in EP 0 392 059 B1. Accordingly, the synthesis of 1-formamido-3,5-dimethyladamantane, which is used for the manufacture thereof, takes place until now by a halogenation of 1,3-dimethyladamantane and subsequent formamidation. Afterwards, 1-formamido-3,5-dimethyladamantane is hydrolyzed to the amine by means of diluted hydrochloric acid.

However, starting from 1,3-dimethyladamantane, this synthesis method requires three synthesis steps in order to arrive at memantine: halogenation, formamidation, and acidic hydrolysis. Thereby, the use of poisonous, elemental chlorine or bromine in excess is required; this causes additional costs for waste disposal and may lead to undesired by-products.

Thus, the problem of the invention was to provide a method for the formamidation of 1,3-dimethyladamantane, which is simpler and which can be carried out with less poisonous or expensive reagents.

In the international patent application WO 2006/010362 A1, a method for preparing derivatives of 3,5-substituted 1-aminoadamantane has already been described in which a 1,3-disubstituted adamantane derivative is suspended in $HNO_3$ and $H_2SO_4$, and which is reacted with a nitrile after the addition of oleum. In contrast, in the method according to the invention, the preparation of 1-formamido-3,5-dimethyladamantane takes place only in two reaction steps by direct formamidation of 1,3-dimethyladamantane with formamide in concentrated acids.

Preferred are 30-70%, in particular 65% nitric acid and 90-100%, however in particular 95-98% sulfuric acid. However, also 85-100% phosphorus acid, perchloric acid, disulfuric acid or chlorosulfuric acid can be employed. In general, the reaction takes place at 40° C. up to 50° C., however preferably at 0° C. In the method according to the invention, mostly yields of 40-95% are achieved.

Said method is not only characterized by being free of halides, however has also a more favourable impurity profile, because it runs in high yields and only with a small amount of by-products, and thereby even tolerates impurities in the starting materials. According to GC-MS, in the formamidation only non-reacted educt as well as 3,5-dimethyladamantane-1-ol could be detected as by-products.

Even a preparation of the starting material in situ from cheap precursors is possible so that the desired end product is obtainable in a "one pot" method. Thereby, 1,3-dimethyladamantane to be reacted with formamide is obtained in situ from a hydrocarbon having the empirical formula $C_{12}H_{20}$ by cationic rearrangement under comparable reaction conditions, which are also applied for the formamidation. For example, one obtains the precursors by means of perhydrogenation of acenaphthene, acenaphthalene or methylcyclopentadiene dimer. Subsequent, the formamidation of the produced dimethyladamantane is carried out under acid conditions in the same reaction vessel.

The treatment of perhydrogenated methycyclopentadiene dimer with concentrated acids allows the manufacture of the starting material 1,3-dimethyladamantane in situ prior to the formamidation according to the following reaction:

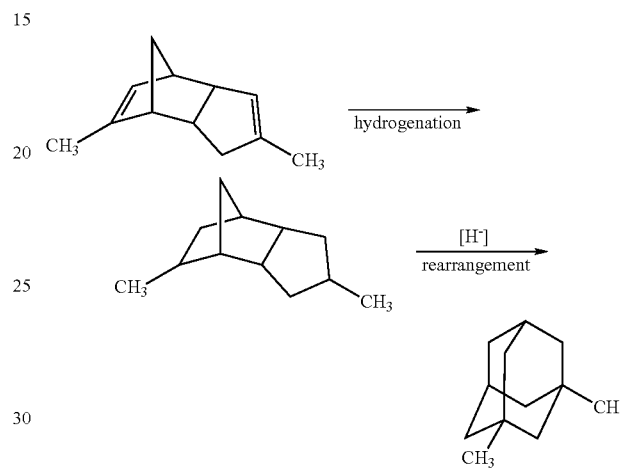

The method described in the international application PCT/DE2005/001304 is based on the generation of carbocations in concentrated acids, which can be scavenged by a nucleophile such as a nitrile, and which are converted to the corresponding 1-amidoadamantane derivatives in aqueous processing according to the following reaction:

On contrast, the method according to the invention for preparing 1-formamido-3,5-dimethyladamantane allows milder reaction conditions and the complete avoidance of the application of oleum or 100% nitric acid. Furthermore, formamide is used as nucleophile, whereby as reaction product 1-formamido-3,5-dimethyladamantane is produced that can be hydrolyzed under considerably milder conditions compared to other amides. So, for example, 1-acetamido-3,5-dimethyladamantane is cleaved by heating NaOH for several hours in aqueous or alcoholic base or in concentrated hydrochloric acid (36-37%) to the free 1-amino-3,5-dimethyladamantane, whereas the cleavage of the formamide already succeeds with diluted hydrochloric acid within two hours at 100° C.

The invention is specified by the following examples:

EXAMPLE 1

Synthesis of 1-formamido-3,5-dimethyladamantane

In sequence, 4 mL 65% technical nitric acid and then within three hours 50 mL 98% technical sulfuric acid are added to 6.572 g (40 mmol) 1,3-dimethyladamantane at 0° C. It is stirred over night at 0° C. and the mixture is poured at 0° C. onto 100 mL formamide in a round bottom flask which is provided with a drying tube. This mixture is stirred for 30 min at 0° C. and for 90 min at room temperature and 200 mL dichloromethane and 200 mL water are added. After phase separation, the organic phase is washed with water and 2% $NaHCO_3$-solution, is dried, over $Na_2SO_4$ and is freed from solvents at the rotary evaporator. The remaining oil is chromatographically purified ($SiO_2$, $CHCl_3$/acetone (20:1), $R_f$=0.39). 7.41 g (89.3%) of the formamide are obtained as a nearly colourless solid.

$^1$H-NMR ($CDCl_3$, TMS, 400.13 MHz): δ=0.87 ppm, s, 6H; 1.15 ppm, s, 2H; 1.2-1.35 ppm, m, 4H; 1.35-1.55 ppm, m, 4H; 1.65-1.78 ppm, m, 2H; 2.10-2.27 ppm, m, 1H; 5.90 and 7.21 ppm; each br., s, 1H; 8.02, 8.20 and 8.27 ppm, each s., 1H.

$^{13}$C-NMR ($CDCl_3$, TMS, 100.61 MHz): δ=29.46, 30.01, 32.00, 40.21, 41.85, 47.63, 49.94, 51.83, 160.15/162.24 ppm.

MS: m/z=207 (M$^+$), 192, 150, 136, 106, 91, 79.

EXAMPLE 2

Hydrolysis of 1-Formamido-3,5-dimethyladamantane to 1-Amino-3,5-dimethyladamantane hydrochloride (Memantine)

0.02 mmol 1-formamido-3,5-dimethyladamantane (4.14 g) are refluxed for 24 hours in 100 mL 15% hydrochloric acid. After cooling, the precipitate is filtered off, is dissolved in methanol and is precipitated by addition of ethyl acetate (yield 80%).

The invention claimed is:

1. A process for preparing 1-formamido-3,5-dimethyladamantane by direct formamidation of 1,3-dimethyladamantane, wherein 1,3-dimethyladamantane is reacted with formamide in concentrated acids, provided that the concentrated acid is not a $SO_3$-containing sulfuric acid or 100% nitric acid, wherein 30-70% nitric acid and 90-100% sulfuric acid are employed as the concentrated acids.

2. The process of claim 1, wherein 1,3-dimethyladamantane is prepared from a hydrocarbon precursor having the empirical formula $C_{12}H_{20}$ by cationic rearrangement in a separate reaction or in situ prior to the direct formamidation.

3. The process of claim 1, wherein the process further comprises conversion of 1-formamido-3,5-dimethyladamantane to 1-amino-3,5-dimethyladamantane by hydrolysis.

4. The process of claim 3, wherein the hydrolysis takes place with aqueous hydrochloric acid.

* * * * *